United States Patent [19]
Bailey

[11] Patent Number: 5,090,904
[45] Date of Patent: Feb. 25, 1992

[54] AUTOCLAVABLE AIR POLISHER HANDPIECE

[75] Inventor: Ronald L. Bailey, Harvester, Mo.

[73] Assignee: Young Dental Manufacturing Company, Creve Coeur, Mo.

[21] Appl. No.: 619,039

[22] Filed: Nov. 28, 1990

Related U.S. Application Data

[63] Continuation-in-part of Ser. No. 477,748, Feb. 9, 1990.

[51] Int. Cl.$^5$ ................................. A61C 3/02
[52] U.S. Cl. ...................................... 433/88
[58] Field of Search ........... 433/80, 81, 88, 84, 433/85, 126; 51/427, 439

[56] References Cited

U.S. PATENT DOCUMENTS

| | | | |
|---|---|---|---|
| 3,295,514 | 1/1967 | Hein et al. | 128/2.1 |
| 3,593,423 | 7/1971 | James et al. | 32/22 |
| 3,972,123 | 8/1976 | Black | 32/58 |
| 4,174,571 | 11/1979 | Gallant | 433/216 |
| 4,214,871 | 7/1980 | Arnold | 433/216 |
| 4,412,402 | 11/1983 | Gallant | 51/439 |
| 4,522,597 | 6/1985 | Gallant | 433/216 |
| 4,608,018 | 8/1986 | Ghedini et al. | 433/88 |
| 4,676,749 | 6/1987 | Mabille | 433/88 |
| 4,776,794 | 10/1988 | Meller | |
| 4,820,152 | 4/1989 | Warrin et al. | 433/86 |
| 4,957,483 | 9/1990 | Gonser et al. | 433/126 |

FOREIGN PATENT DOCUMENTS 1416921 10/1968 Fed. Rep. of Germany.

*Primary Examiner*—Cary E. O'Connor
*Attorney, Agent, or Firm*—Polster, Lieder, Woodruff and Lucchesi

[57] ABSTRACT

An autoclavable air polisher handpiece having an insert which is removably inserted in a jacket having an air polisher tip. The insert connects an air/abrasive tube and water tube to the handpiece. The jacket and tip may be disconnected from the insert body for autoclaving the jacket and tip without the necessity of disconnecting the tubes from the insert.

16 Claims, 1 Drawing Sheet

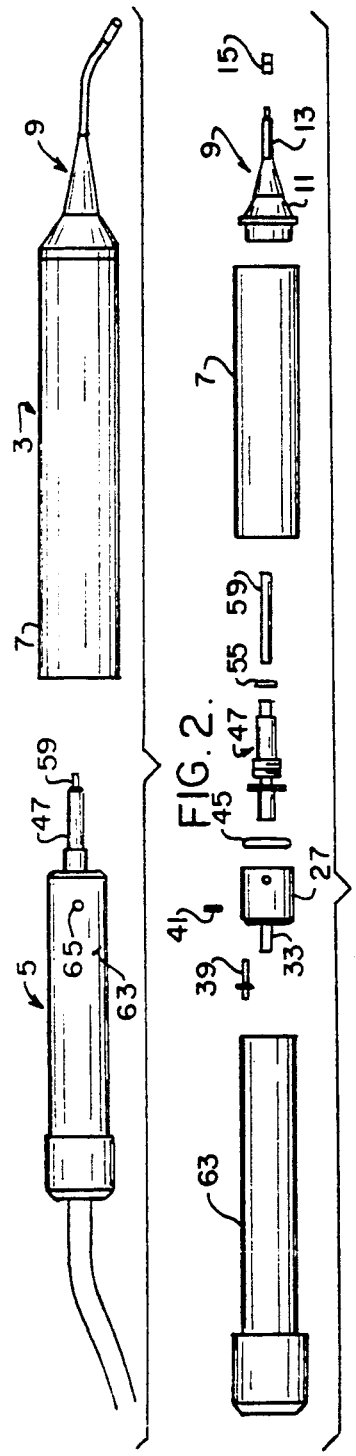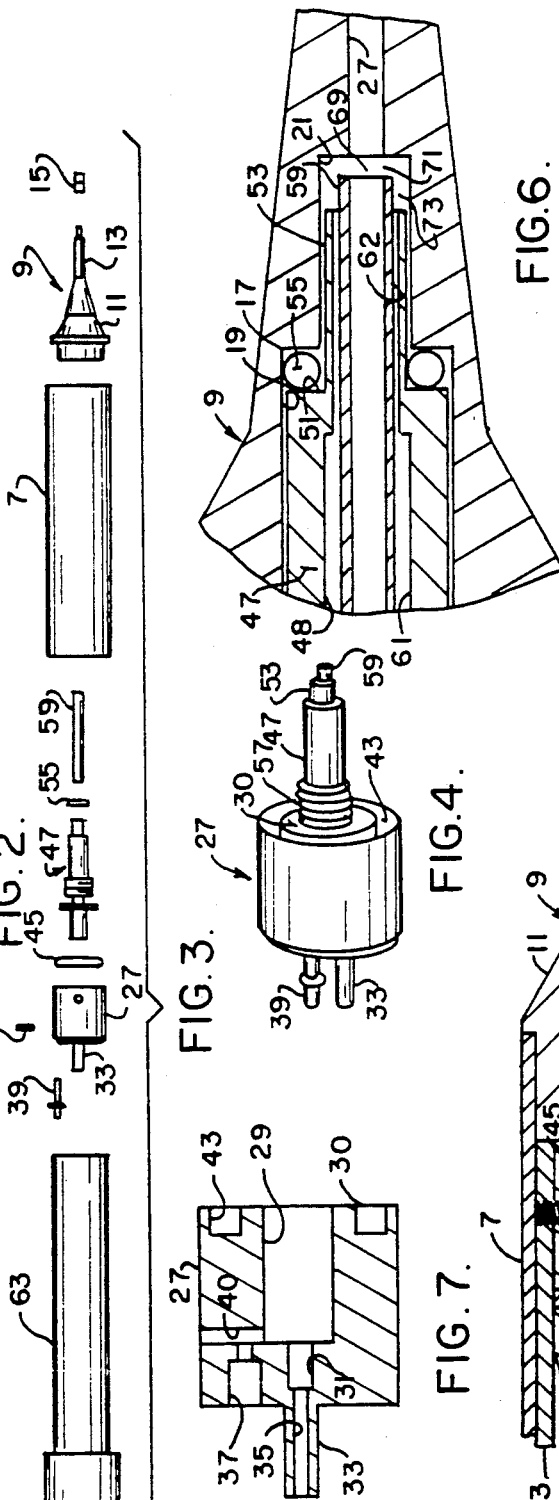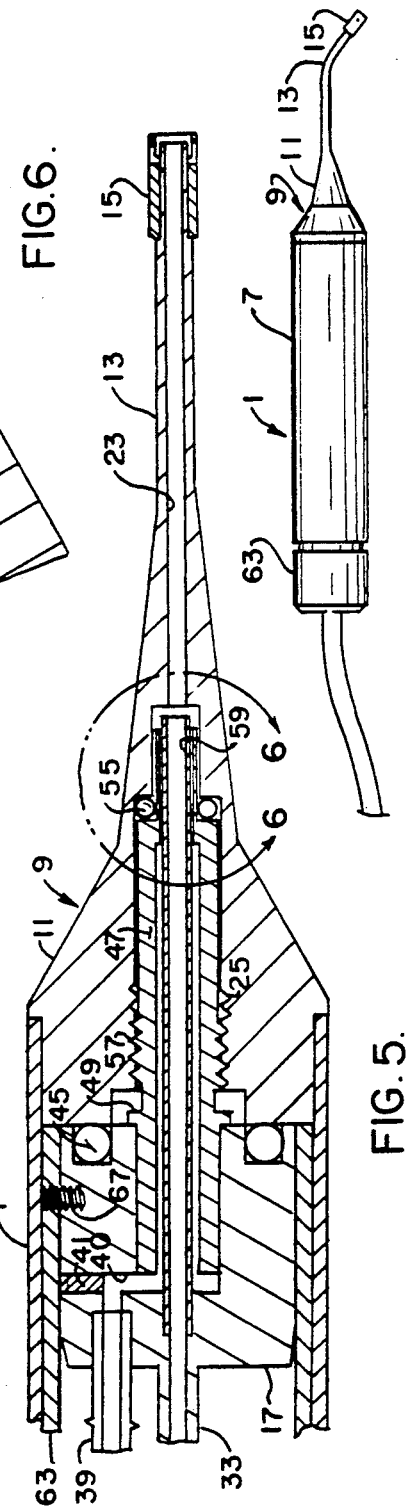

AUTOCLAVABLE AIR POLISHER HANDPIECE

CROSS-REFERENCE TO RELATED APPLICATIONS

This is a continuation-in-part of co-pending application Ser. No. 477,748 filed Feb. 9, 1990 pending which is incorporated herein by reference.

BACKGROUND OF THE INVENTION

This invention relates to an autoclavable air polisher handpiece, and, in particular, to a handpiece which is autoclavable without the need for disconnecting water and air/abrasive supply tubes.

An air polisher handpiece cleans by abrading teeth with soluble abrasive in the presence of a liquid. The handpiece is commonly connected to a source of liquid and abrasive by flexible tubing.

A preferred method of cleaning air polisher handpieces is to autoclave the handpiece after teeth cleaning operations. In my co-pending application Ser. No. 477,748, filed Feb. 9, 1990, which is incorporated herein by reference, I disclosed a new air polisher head To autoclave that head, the air and liquid tubing had to be disconnected from the handpiece to clean the handpiece. The constant separation of the tubing from this type of handpiece will lead to a poor joining of the tubing to the handpiece. Further, the need to disconnect the tubing makes the cleaning process more difficult and time consuming.

SUMMARY OF THE INVENTION

One object of the present invention is to provide an air polisher handpiece which eliminates the necessity of disconnecting tubing from the handpiece in order to autoclave the handpiece.

Another object is to provide such a head which produces less aerosol overspray than presently known cleaners and is therefore neater, more convenient for the hygienist using it, more comfortable for the patient, and more sanitary.

Another object is to provide such a head which may focus on a very small area of a tooth.

Another object is to provide such a head which is simple to manipulate in a patient's mouth.

Another object is to provide such a head which requires very little water to clean effectively, but which wets the abrasive particles sufficiently to prevent the build-up of dry powder on the tooth and to leave a minimum of gritty residue in the patient's mouth.

Another object is to provide such a head which resists clogging in normal use and also when its nozzle is pressed against a tooth or tissue.

Another object is to provide such a head which minimizes erosion to the head by the abrasive.

Another object is to provide a head which cleans effectively independent of its distance, within a normal operating range of about one to five millimeters from the tooth and without requiring movement with respect to the tooth.

Another object is to provide such a handpiece which will effectively clean a patient's teeth.

Other objects of this invention will be apparent to those skilled in the art in light of the following description and accompanying drawings.

In accordance with the invention generally stated, there is provided a dental cleaner for cleaning teeth with soluble abrasive particles in the presence of a liquid. The cleaner includes an insert having a pair of passages therethrough and flexible conduit connecting means for connecting the passages to a supply of an abrasive laden gas and a supply of liquid. The cleaner also includes an outer portion including a dental cleaning tip having a passage therethrough which communicates with the insert passages The outer portion removably receives the insert whereby the outer portion can be autoclaved without removing the tubes from the insert. Preferably, the outer portion includes a jacket to which the tip is connected. The jacket at least partially covers the insert.

In the preferred embodiment, the handpiece is formed to operate in substantially the same manner as the handpiece described in my aforesaid application Ser. No. 477,748. The insert includes a hollow post which axially receives a tube. The tube is spaced from the inside of the post to define an annular passage. The tube defines one of the insert passages, and the annular passage defines another of the insert passages. The cross-sectional area of the tube is preferably substantially larger than the cross-sectional area of the annular passage, to ensure that the flow of gas/abrasive through the tube dominates the flow of liquid through the annular passage, even though the supply pressure of each is approximately the same. The tube preferably extends beyond the post.

The tip of the cleaner includes a passageway therethrough. The passageway is stepped to define a rear section, a middle section, and a forward section. The forward section defines a nozzle. The rear section receives the insert post, and the middle section receives the open ends of the post and the tube. The insert tube and the tip passageway forward section are coaxial and have the same inner diameter so that they form a single passageway with a small gap in it. The insert tube, the tip passageway middle section, and the gap define an annular aperture and an annular fluid reservoir which surrounds the annular aperture. The annular aperture is short relative to the diameter of the tube. It therefore performs the same function as the aperture in the tube of my aforesaid copending application, Ser. No. 477,748.

BRIEF DESCRIPTION OF THE DRAWINGS

In the drawings, FIG. 1 is a view in side elevation of an air polisher handpiece of the present invention;

FIG. 2 is an exploded view of the handpiece;

FIG. 3 is a further exploded view of the handpiece;

FIG. 4 is a perspective view of a tube connector body of the handpiece;

FIG. 5 is a fragmentary cross-sectional view, on an enlarged scale, of the handpiece;

FIG. 6 is a further enlarged fragmentary cross-sectional view taken along line 6—6 of FIG. 5; and FIG. 7 is a cross-sectional view of the connector body on an enlarged scale.

DESCRIPTION OF THE PREFERRED EMBODIMENT

Referring initially to FIGS. 1-3, reference numeral 1 generally refers to an air polisher handpiece of the present invention. Handpiece 1 includes an autoclavable outer portion 3 which removably receives an insert 5. Outer portion 3 includes a stainless steel jacket 7 and a stainless steel air polisher tip 9. Tip 9 is formed separately from jacket 7 and is force fitted therein. Tip 9 includes a multiply tapered head part 11 and a nozzle part 13. Nozzle part 13 is about 0.65" long and is bent by about 30° at the center thereof.

Nozzle part 13 is fitted with a blow-by tip 15. The blow-by tip 15 may be the one described in my aforesaid co-pending application. However, it is preferably modified as shown in FIG. 5 to seat against a shoulder 14 on the nozzle part 13, with relief holes 16 positioned upstream of the open end of the nozzle part 13. The open end of the tip 15 is stepped outward at the centers of the holes 16 to an inner diameter of 0.007". Tip 9 has a stepped passageway 17 therethrough defining three portions, a rear wide section 19, a middle section 21, and a narrow section 23 which extends through nozzle 13. Rear portion 19 of passageway 17 is threaded as at 25, remote from the middle section.

Insert 5 includes a stainless steel connector body 27 having an axial bore 29 extending inwardly from a planar front surface 30 thereof. (FIG. 7) Bore 29 has a counter bore 31 in the center thereof. A post 33 in the center of connector body 27, at the rear thereof, has a passageway 35 which communicates with counter bore 31 and bore 29. A second bore 37, above post 33, receives a hollow barb 39. Bore 37 communicates with a vertical passage 40 which is partially plugged with a plug 41. (FIG. 5) Passageway 40 is perpendicular to bore 29 and to bore 37. Post 33 connects passageway 35 to a source of abrasive laden gas, preferably finely-divided sodium bicarbonate in air, by means of a flexible tube. Barb 39 connects passageway 37 to a source of liquid, preferably water, again by means of a flexible tube. Both the gas and the liquid are preferably pressurized to about 30 psi. Preferably post 33 and barb 39 are attached to the control box of my copending application Ser. No. 477,609, filed Feb. 9, 1990, or to the control box of my application Ser. No. 619,037, filed Nov. 28, 1990. Body 27 also includes an annular channel 43, on face 30, spaced from bore 29 which receives an O-ring 45.

Bore 29 receives a stainless steel hollow post 47 having a central bore 48 therethrough. Post 47 includes a flange 49 which contacts front surface 30 of connector body 27. Flange 49 is positioned on post 47 such that when post 47 is inserted in bore 29, the rear of post 47 is approximately even with the forward surface of vertical passageway 40. The outer surface of post 47 is stepped down at the forward end thereof to form a shoulder 51 and a narrow tip portion 53. The outer diameter of post 47 is reduced to about 0.070" from about 0.149" at step 51. The central bore 48 of post 47 is similarly stepped down as at 52 so that the bore is narrower in post tip portion 53. Step 52 reduces central bore 48 to an inner diameter of 0.0571" from 0.080". An O-ring 55 is seated on post shoulder 51. Post 47 includes threads 57 forward of flange 49.

Post 47 receives an air tube 59 which extends beyond post 47 to be seated in counter-bore 31. The outer diameter of air tube 59 is about 0.050" which is about 0.030" smaller than the inner diameter of post bore 48. The outer diameter of air tube 59 is about 0.007" smaller than the inner diameter of post tip 53.

Post 47 and air tube 59 create an annular passageway 61 between it and the inner surface of post 47. Passageway 61 communicates with passage 40 and hence the liquid supply. The inner and outer diameters of passageway 61 are about 0.050" and 0.080", respectively. Annular passageway 61 thus has a width of 0.015" and a cross-sectional area of 0.0031 in2. Passage 61 narrows in tip 53 at step 52 to form an annular passage 62. The outer wall of passage 62 has a diameter of 0.0571" and the inner wall has a diameter of 0.0500". Thus passage 62 has a clearance of about 0.0035" and a cross-sectional area of about 0.0006 in2. Air tube 59 extends 0.080" beyond the tip portion 53 of post 47.

Air tube 59 has an inner diameter of 0.033", which is equal to the inner diameter of passageway 23 in nozzle 13. Air tube 59 and passageway 23 thus have cross-sectional areas of about 0.0009 in2.

Connector body 27 is received in a sleeve 63 made of Delrin. Sleeve 63 has a screw hole 65 which is aligned with a screw hole 67 in body 27. A set screw is passed through screw holes 65 and 67 to secure body 27 in sleeve 63.

Insert 5, which comprises sleeve 63, connector body 27 post 47, and air tube 59 is received in outer portion 3. Specifically, post 47 is received in the wider portion 19 of head passageway 17, and post tip 53 and air tube 59 are received in the middle section 21. Post threads 57 mate with threads 25 of head 11 to removably secure insert 5 to outer portion 3.

As can be seen in FIG. 6, the length of air tube 59 is such that when handpiece 1 is assembled, the air tube 59 and passageway 23 are coaxial, and a gap 69 is formed between air tube 59 and nozzle bore 23. Gap 69 is about 0.015" long. This is smaller than the inner diameters of air tube 59 and nozzle 23. Bore 23 is about 1.086" long and air tube 59 is about 1.155" long. Thus, nozzle bore 23 and air tube 59 in essence form a single tube 2.241" long with an 0.015" annular aperture 71 having an effective surface area of 0.00155 in2. This annular aperture is surrounded by an annular reservoir 73. Passageway 62 opens into reservoir 73 at its exit 74.

It will be seen that the effective surface area of the annular aperture is larger than the cross-sectional area of the annular passage 62. The flow-limiting restriction is thus the annular passage 62, and water does not tend to collect in great quantities in reservoir 73.

In operation, the air and entrained abrasive pass through post 33 and air tube 59 to nozzle 23 and out the head. Water enters the body 27 through barb 39 and passes through passageway 40 to annular passageways 61 and 62 into the annular reservoir 73. The pressure of the water forces the water in reservoir 73 through aperture 71 to inject it into the stream of abrasive laden air to form a mist of water and abrasive particles carried by the air. The air then carries the mist through nozzle bore 23 and out the end of the nozzle as a focused stream.

Exit 74 of passageway 62 effectively meters the flow of water into gap 69 to insure that the air/abrasive stream in air tube 59 is dominant. The water essentially dribbles out of the passageway 62 into reservoir 73. With the air stream dominant, water entry gap 71 does not detrimentally affect abrasive pick-up and there is not sufficient water present to dissolve the abrasive particles. Thus, the integrity of most of the abrasive particles is maintained and there is sufficient abrasive to effectively clean teeth.

Air tube 59 can flex somewhat, and the water emerging from the annular passageway 62 tends to be predominantly at one side of the passageway 62. Thus, water tends to enter the air/abrasive stream from one side of the stream, and wetting of the abrasive particles is believed to be greater at one side of the stream than at the other. Nonetheless, all or most of the particles are wetted to some degree, even though very little water is used. Fine water droplets attach to abrasive particles.

Most particles are not sufficiently wetted to dissolve them before they reach a tooth surface. Thus, the abrasive particles maintain their effectiveness as cleaners, and there is very little aerosol cloud formation Therefore, a majority of the particles act as cleaners.

Because the abrasive particles are attached to fine droplets of water, and because the mist impinging on the patient's teeth is focused to a narrow spot, the air-polisher of the present invention produces far less aerosol overspray or plume than do previously known air-polishers. Because the abrasive is wetted, a hygienist can clean a single spot without having to move the head to wash away piles of abrasive. Thus, the manner of operation is very similar to that disclosed in my aforesaid co-pending application Ser. No. 477,748.

The outer portion 3, comprising sleeve 7, head 9, and blow-by tip 15, is autoclavable. Because insert 5 is removeably connected to head 9, after a cleaning operation, the outer portion 3 may be easily removed from insert 5 so that outer portion 3 may be autoclaved. As the source of liquid and gas are connected to the insert 5, there are no flexible tubes that need to be removed in order to clean the handpiece 1. Because the insert 5 is never exposed to a patient's mouth, it need only be wiped down between uses. For example, a disinfectant may be used.

If the insert 5 and outer portion 3 are connected when the handpiece 1 is activated or deactivated, air and abrasive from air tube 59 may enter liquid passages 61 and 62. To prevent this, the source of air and liquid are preferably activated with insert 5 separated from outer portion 3. The same is true for deactivating the air and water supplies.

Numerous variations, within the scope of the appended claims, will be apparent to those skilled in the art in light of the foregoing description and accompanying drawings. For example, the inner tube outer diameter could be same as the inner diameter as post tip 58, thereby closing off annular aperture 61. A small aperture could then be created in post 47 through which the liquid would be injected into air tube 59. This variation would make this handpiece operate in the exact same manner as the handpiece disclosed in my aforementioned co-pending application. The outer portion 3 may be made from any material which may be autoclaved. Similarly, the sleeve 63 may be made from any material which can be easily wiped down. These examples are merely illustrative.

Having thus described the invention, what is claimed and desired to be secured by Letters Patent is:

1. A dental cleaner for cleaning teeth with soluble abrasive particles in the presence of a liquid comprising an insert having passage means therethrough and flexible conduit connecting means for connecting said passage means to tubes which communicate with a supply of an abrasive laden gas and a supply of a liquid; and an outer portion including a dental cleaning tip having passage means therethrough which communicate with said insert passage means, and a jacket to which said tip is connected; said insert being removably connected to and completely covered by said outer portion whereby said outer portion can be autoclaved without removing said tubes from said insert.

2. The dental cleaner of claim 1 wherein said insert is rotatably connected to said outer portion.

3. The dental cleaner of claim 2 wherein said insert is rotatably connected to said tip.

4. A dental cleaner for cleaning teeth with soluble abrasive particles in the presence of a liquid comprising an insert having a pair of passages therethrough and flexible conduit connecting means for connecting said passages to a pair of tubes which communicate with a supply of an abrasive laden gas and a supply of a liquid; and an outer portion including a dental cleaning tip having a passage therethrough which communicates with said insert passages, said outer portion removably receiving said insert whereby said outer portion can be autoclaved without removing said tubes from said insert; said insert including a hollow post which axially receives a tube, said tube being spaced from the inside of said post, said tube defining one of said insert passages, said space between said tube and said post defining another of said insert passages.

5. The dental cleaner of claim 4 wherein said tube extends beyond said post.

6. The dental cleaner of claim 5 wherein said tip includes a passageway therethrough, said passageway being stepped to define a rear section, a middle section, and a forward section, said forward section defining a nozzle; wherein said rear section receives said post and said middle section receives said tube.

7. The dental cleaner of claim 6 wherein said insert tube is spaced form said tip passageway forward section to define a gap.

8. The dental cleaner of claim 7 wherein said insert tube and said passageway forward section have the same inner diameter.

9. The dental cleaner of claim 8 wherein said insert tube, said tip passageway forward section and said gap define an annular aperture and an annular fluid reservoir surrounding said aperture.

10. A connector body for removably connecting a liquid supply tube and an abrasive laden gas supply tube to a cleaning tip of an air polisher, said connector body including a forward bore which receives a hollow post; said post receiving a hollow tube, said hollow tube having an outer diameter which is smaller than the inner diameter of said hollow post; said hollow tube defining a first passageway of said connector body; the space between said hollow tube and said hollow post defining a second passageway through said connector body; said liquid supply tube communicating with one of said first and second connector body passageways, said abrasive laden gas supply tube being connected to the other of said first and second connector body passageways, said passageways communicating with a passageway in said cleaning tip.

11. A connector body for removably connecting a liquid supply tube and an abrasive laden gas supply tube to a cleaning tip of an air polisher, said connector body including a forward bore which receives a hollow post; said post receiving a hollow tube, said hollow tube having an outer diameter which is smaller than the inner diameter of said hollow post; said hollow tube defining a first passageway of said connector body; the space between said hollow tube and said hollow post defining a second passageway through said connector body; said liquid supply tube communicating with one of said first and second connector body passageways, said abrasive laden gas supply tube being connected to the other of said first and second connector body passageways, said passageways communicating with a passageway in said cleaning tip; said post having an internal step near a forward end thereof so that said second passageway in said connector body narrows near a forward end thereof.

12. The connector body of claim 11, wherein said tube extends beyond said post.

13. A dental cleaner for cleaning teeth with soluble abrasive particles in the presence of a liquid comprising a connector having a pair of passages therethrough and flexible conduit connecting means for connecting said passages to tubes which communicate with a supply of an abrasive laden gas and a supply of a liquid; a jacket; and a dental cleaning tip connected to said jacket, said cleaning tip having a single passage therethrough which communicates with both said connector passages, said connector being removably connected to said tip whereby said tip and said jacket can be autoclaved without removing said tubes from said connector.

14. The dental cleaner of claim 13 wherein said connector is rotatably connected to said tip.

15. A dental cleaner for cleaning teeth with soluble abrasive particles in the presence of a liquid comprising an insert having passage means therethrough and tube connecting means for connecting said passage means to tubes which communicate with a supply of an abrasive laden gas and a supply of a liquid;

an outer portion including a hollow jacket and a dental cleaning tip connected to said hollow jacket, said tip having passage means therethrough which communicate with said insert passage means; and means rendering said outer portion autoclavable, said means including means on said insert for removably, rotatably connecting said insert to said outer portion, whereby said outer portion can be autoclaved without removing said tubes from said insert.

16. A method for autoclaving a dental cleaner which cleans by abrading a surface with soluble abrasive particles in the presence of a liquid, said dental cleaner comprising an outer portion having a hollow jacket and a tip connected to said jacket and having a passage therethrough and a connector having passage means therethrough and connecting means for connecting said passage means to tubes which communicate with a supply of an abrasive laden gas and a supply of a liquid, said connector being rotatably, removably connected to said outer portion; said method comprising steps of rotatably disconnecting said insert from said outer portion, removing said insert from said outer portion, and autoclaving said outer portion.

* * * * *